US010625942B2

(12) United States Patent
Hou

(10) Patent No.: US 10,625,942 B2
(45) Date of Patent: Apr. 21, 2020

(54) RUBBER SELECTION METHOD

(71) Applicant: The Yokohama Rubber Co., LTD., Minato-ku, Tokyo (JP)

(72) Inventor: Gang Hou, Hiratsuka (JP)

(73) Assignee: The Yokohama Rubber Co., LTD. (JP)

( * ) Notice: Subject to any disclaimer, the term of this patent is extended or adjusted under 35 U.S.C. 154(b) by 0 days.

(21) Appl. No.: 16/095,669

(22) PCT Filed: Feb. 22, 2017

(86) PCT No.: PCT/JP2017/006494
§ 371 (c)(1),
(2) Date: Oct. 22, 2018

(87) PCT Pub. No.: WO2017/183282
PCT Pub. Date: Oct. 26, 2017

(65) Prior Publication Data
US 2019/0127150 A1   May 2, 2019

(30) Foreign Application Priority Data
Apr. 22, 2016 (JP) .................. 2016-085951

(51) Int. Cl.
*G01N 3/00* (2006.01)
*B65G 15/32* (2006.01)
(Continued)

(52) U.S. Cl.
CPC ............... *B65G 15/32* (2013.01); *G01N 3/30* (2013.01); *G01N 3/303* (2013.01); *G01N 3/48* (2013.01); *B65G 2812/02198* (2013.01)

(58) Field of Classification Search
CPC .......... B65G 15/32; B65G 2812/02198; G01N 3/30; G01N 3/303; G01N 3/48
(Continued)

(56) References Cited

U.S. PATENT DOCUMENTS 4,313,337 A * 2/1982 Myint ...................... G01N 3/34
73/12.13
4,429,068 A * 1/1984 Nakahira ............. A43B 13/181
152/310

(Continued)

FOREIGN PATENT DOCUMENTS

JP    H10-260123    9/1998
JP    2010-216852   9/2010
(Continued)

OTHER PUBLICATIONS

International Search Report for International Application No. PCT/JP2017/006494 dated May 23, 2017, 4 pages, Japan.

*Primary Examiner* — Max H Noori
(74) *Attorney, Agent, or Firm* — Thorpe North & Western

(57) ABSTRACT

According to the present technology, an impact test in which an impact application member is made to free fall onto a test sample of a plurality of types of rubbers having different physical properties is performed under prescribed test conditions; data for at least one of three items including a loss energy that is absorbed by the test sample when the impact application member collides with the test sample, a thermal energy that is generated at the test sample, and an indentation amount into the test sample by the impact application member is acquired; and an optimal test sample is selected from the respective test samples on a basis of a ranking of the superiority of the respective test samples with respect to the item(s) for which data was acquired.

8 Claims, 7 Drawing Sheets

(51) Int. Cl.
*G01N 3/303* (2006.01)
*G01N 3/48* (2006.01)
*G01N 3/30* (2006.01)

(58) Field of Classification Search
USPC .......................................................... 73/788
See application file for complete search history.

(56) References Cited

U.S. PATENT DOCUMENTS

| | | | |
|---|---|---|---|
| 5,929,316 A * | 7/1999 | Lee ........................ | G01N 3/307 73/12.09 |
| 2004/0040369 A1* | 3/2004 | Hoo Fatt .................. | G01N 3/30 73/12.01 |
| 2013/0160519 A1* | 6/2013 | Zhai ........................ | G01N 3/30 73/12.09 |
| 2017/0292895 A1* | 10/2017 | Hou ........................ | G01M 7/08 |
| 2019/0128786 A1* | 5/2019 | Hou ........................ | G01N 3/303 |

FOREIGN PATENT DOCUMENTS

| | | |
|---|---|---|
| JP | 2011-257187 | 12/2011 |
| JP | 2012-189533 | 10/2012 |
| WO | WO 2016-042999 | 3/2016 |

\* cited by examiner

RUBBER SELECTION METHOD

TECHNICAL FIELD

The present technology relates to a rubber selection method, and more specifically, relates to a rubber selection method which makes it possible to select an appropriate rubber that conforms to the actual use of a target object such as a conveyor belt when selecting a rubber to be used in the target object.

BACKGROUND ART

Various objects to be conveyed, including mineral resources such as iron ore and limestone, are conveyed by a conveyor belt. When the objects to be conveyed are fed onto the upper cover rubber of the conveyor belt, the upper cover rubber is subjected to impact, and when the surfaces of the objects to be conveyed are sharp, the surface of the upper cover rubber may sustain cut damage in some cases.

Various methods for evaluating the impact resistance of a conveyor belt have been proposed in the past (see for example Japan Patent Publication Nos. 2010-216852, 2011-257187 and 2012-189533). Ordinarily, the impact resistance of rubber is evaluated by understanding the damage condition of a test sample into which an impact application member such as a weight has collided.

The impact resistance of the upper cover rubber differs depending on the rubber characteristics, usage environment, etc. Therefore, the appropriate rubber for the upper cover rubber needs to be selected with consideration of the impact resistance during actual use of the conveyor belt.

SUMMARY

The present technology provides a rubber selection method which makes it possible to select an appropriate rubber that conforms to the actual use of a target object such as a conveyor belt when selecting a rubber to be used in the target object.

One aspect of the present technology is a rubber selection method for selecting a rubber for use in a target object to be used while being collided against by a colliding object; wherein an impact test in which an impact application member is made to free fall onto a test sample of a plurality of types of rubbers having different physical properties is performed under prescribed test conditions; data for at least one of three items including a loss energy that is absorbed by the test sample when the impact application member collides with the test sample, a thermal energy that is generated at the test sample, and an indentation amount into the test sample by the impact application member is acquired; and a specific test sample is selected from the plurality of types of test samples on the basis of a ranking of the superiority of the plurality of test samples with respect to the item(s) for which data was acquired.

Another aspect of the present technology is a rubber selection method for selecting a rubber for use in a target object to be used while being collided against by a colliding object; wherein an impact test in which an impact application member is made to free fall onto a test sample of a plurality of types of rubbers having different physical properties is performed under prescribed test conditions; data for at least one of three items including a loss energy that is absorbed by the test sample when the impact application member collides with the test sample, a thermal energy that is generated at the test sample, and an indentation amount into the test sample by the impact application member is acquired; a correlation between the item(s) for which data was acquired and a viscoelastic characteristic of each test sample, and a ranking order of the superiority of the plurality of types of test samples with respect to the item(s) for which data was acquired are understood in advance; and when a rubber is to be selected, a specific rubber is selected from the plurality of types of candidate rubbers on a basis of the viscoelastic characteristics of the plurality of types of candidate rubbers, and the correlation and ranking order that are understood in advance.

According to the present technology, when a plurality of types of rubber test samples having different physical properties is used, and an impact application member is made to free fall onto the test samples; data for at least one of three items including a loss energy that is absorbed by the test samples, a thermal energy that is generated at the test samples, and an indentation amount into the test samples by the impact application member is acquired and used. These items are closely related to the durability (impact resistance) of rubber. Therefore, by selecting the optimal rubber on the basis of the ranking (ranking order) of superiority of the plurality of types of test samples with respect to these items, an appropriate rubber that conforms to the actual use of the target object can be selected.

DETAILED DESCRIPTION

Figure 1:
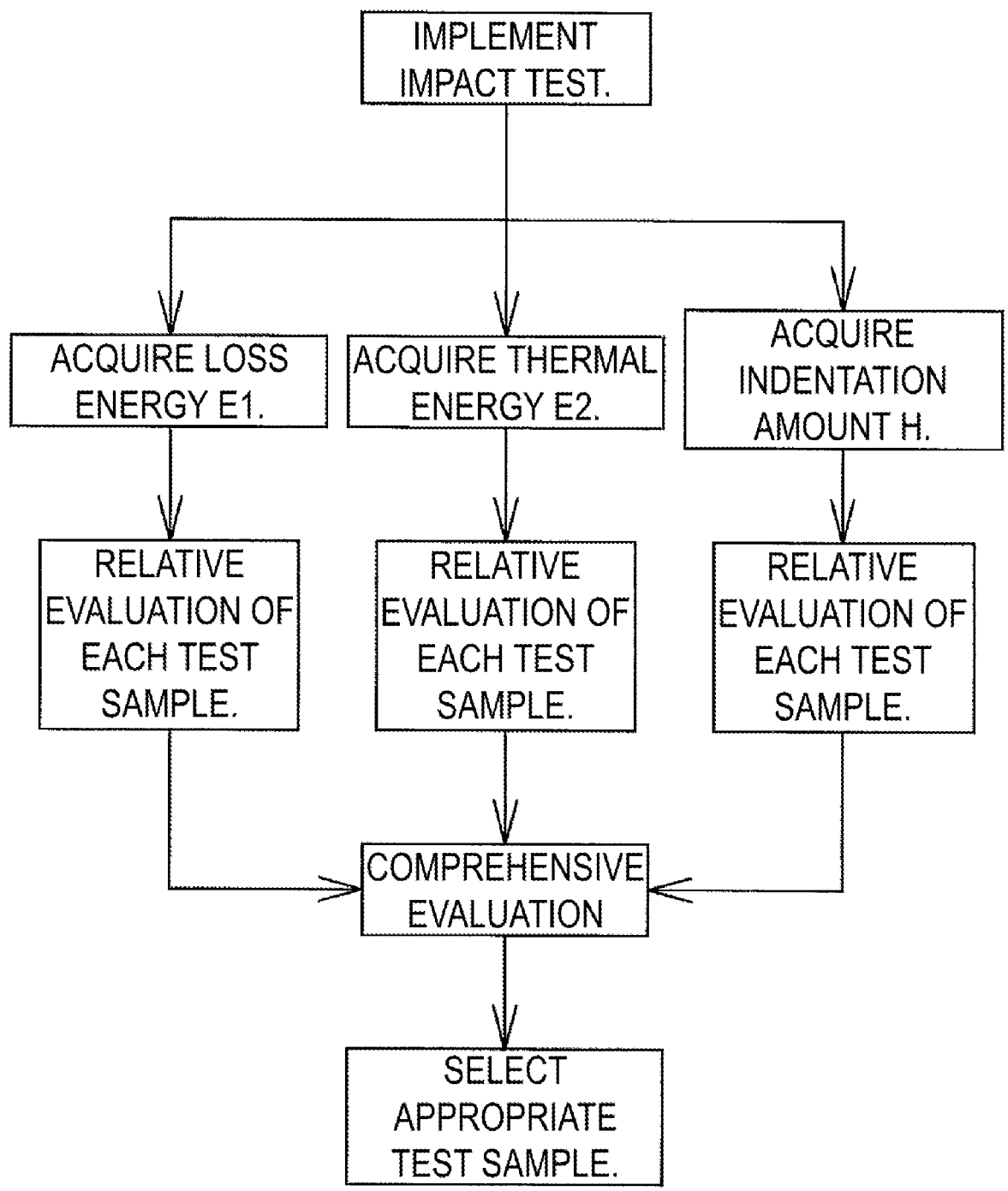
FIG. 1 is an explanatory diagram (flowchart) illustrating the flow when selecting an appropriate rubber according to the present technology.

The rubber selection method of the present technology is described below based on embodiments illustrated in the drawings. With the present technology, a rubber to be used in a target object that is used while being collided against by colliding objects is selected. In the embodiments, a case in which the target object is a conveyor belt, and the rubber to be selected is used in the upper cover rubber of the conveyor belt is described as an example.

In the present technology, an appropriate test sample (rubber) to be used as an upper cover rubber is selected through the procedures illustrated in FIG. 1 from test samples S of a plurality of types of rubbers having different physical properties (viscoelastic characteristics for example).

Figure 2:
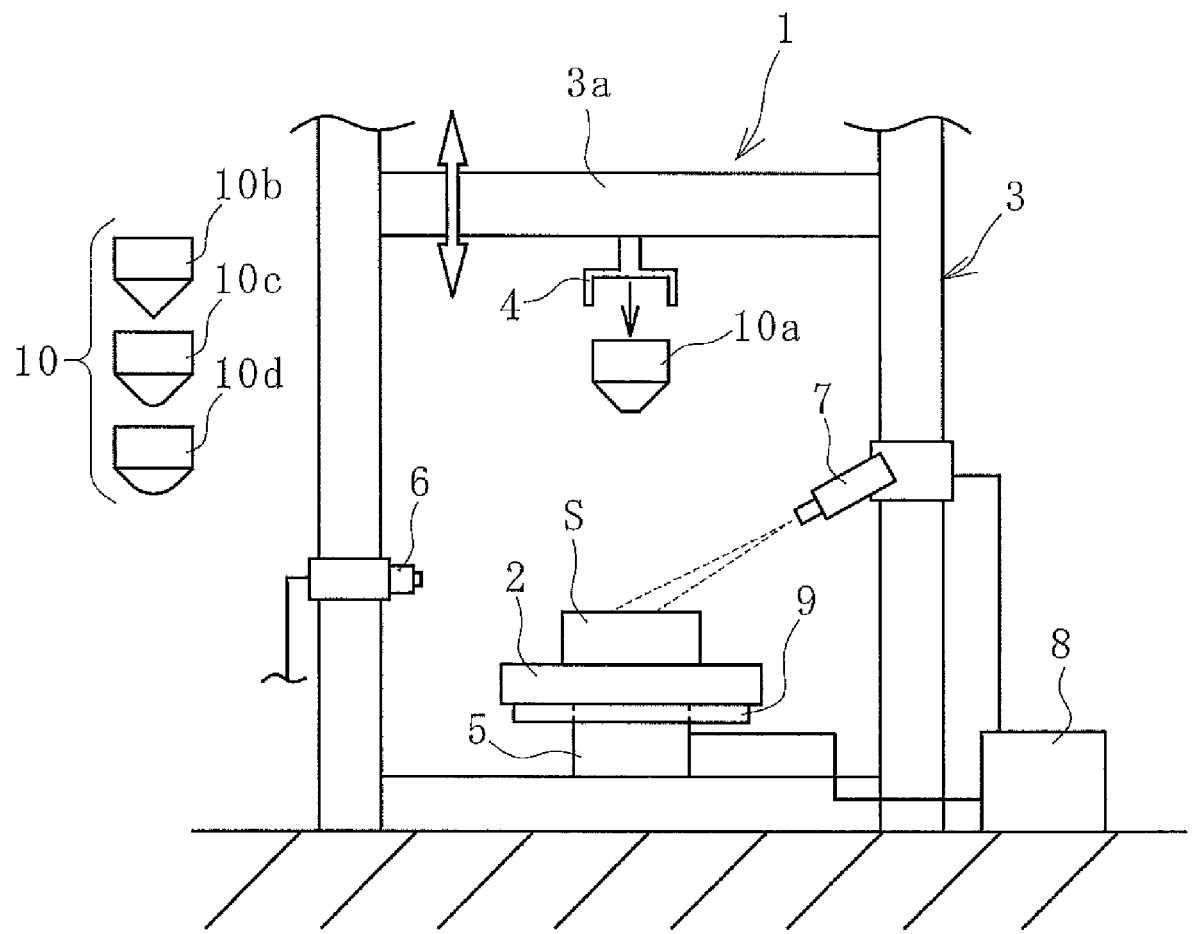
FIG. 2 is an explanatory diagram illustrating a basic structure of an impact test device.

Therefore, first, an impact test device 1 illustrated in FIG. 2 is used to perform, under prescribed test conditions, an impact test in which an impact application member 10 is caused to free fall onto test samples S of a plurality of types of rubbers having different physical properties. The test conditions are preferably conditions which correspond to an environment for a case in which the selected rubber (test sample S) is actually used as an upper cover rubber for a conveyor belt.

According to the present technology, when the impact application member 10 and the test sample S are collided, data for at least one of three items including a loss energy E1 that is absorbed by the test sample S, a thermal energy E2 that is generated at the test sample S, and an indentation amount H into the test sample S by the impact application member 10 is acquired.

The impact test device 1 is provided with: a placement platform 2 on which the test sample S is placed; the impact application member 10 that is caused to free fall onto the sample S; a load meter 5; a displacement meter 6; and a calculation unit 8. The impact test device 1 also has a temperature sensor 7 and a temperature regulator 9.

As the impact application member 10, a plurality of types of impact applying bodies 10a, 10b, 10c, 10d having different specifications such as the lower end shape and the weight are preferably provided. From these plurality of types of specifications, an impact application member 10 of a specification closely resembling the object to be conveyed that will apply an impact to the upper cover rubber in actual use is selected.

At the impact test device 1, a beam portion 3a is extended between frames 3 provided in an upright state, and a holding mechanism 4 is provided from this beam portion 3a. The beam portion 3a can be moved to an optional height position and fixed. The configuration is such that an impact application member 10a detachably held by the holding mechanism 4 can be freely dropped towards the sample S placed on the flat plate shaped placement platform 2 by releasing the holding state.

Figure 3:
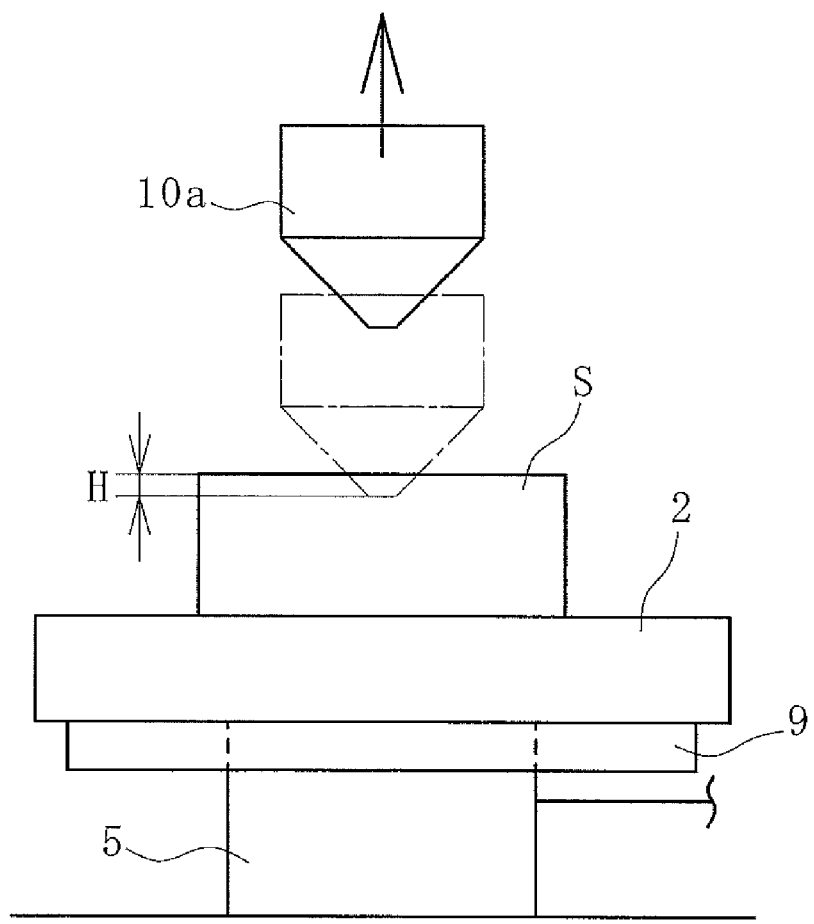
FIG. 3 is an explanatory diagram schematically illustrating a test sample that is deformed by a free falling impact application member.

The load meter 5 is installed below the placement platform 2, and measures the impact force acting on the test sample S. As illustrated by FIG. 3, the displacement meter 6 measures the indentation amount H into the test sample S by the impact application member 10a that was freely dropped and caused to collide with the test sample S. In a case where the lower end shape of the impact application member 10 is sharp, the indentation amount H becomes a flaw depth. Measurement data from the load meter 5 and the displacement meter 6 is input into the calculation unit 8. As the calculation unit 8, various types of computers, etc. can be used.

The temperature sensor 7 measures the surface temperature of the test sample S. The surface temperature measured by the temperature sensor 7 is input into the calculation unit 8. As the temperature sensor 7, thermography and the like can be used.

The temperature regulator 9 sets the temperature of the test sample S to an optional temperature by heating or cooling the test sample S. In the present embodiment, the temperature regulator 9 installed at the bottom surface of the placement platform 2 heats or cools the placement platform 2 to thereby indirectly heat or cool the test sample S and set to an optional temperature. As the temperature regulator 9, in addition, a thermostatic case or the like can be used in which the entire tester is covered with a cover, and the inside of the cover is set to an optional ambient temperature.

The procedures for using this impact test device 1 to acquire the data of each item are as described below.

The test sample S is placed on the placement platform 2 illustrated in FIG. 2. An appropriate impact application member 10a that closely resembles the actual usage conditions of a conveyor belt 11 is selected from the plurality of types of impact applying bodies 10, and is attached to the holding mechanism 4. The beam portion 3a is moved, and the impact application member 10 is set to an appropriate height position (for example, a position of a height h from the surface of the test sample S). The temperature of the test sample S is set to a prescribed temperature by the temperature regulator 9.

Next, the holding of the impact application member 10 by the holding mechanism 4 is released, and the impact application member 10 is freely dropped and caused to collide with the test sample S. At this time, the impact energy E imparted by the impact application member 10 that was freely dropped from the position of the height h from the surface of the sample S is Mgh (E=Mgh). Here, M is the already known mass of the impact application member 10.

The impact force acting on the test sample S is successively measured by the load meter 5 in the collision process from the moment that the impact application member that was caused to free fall contacts the test sample until the impact application member rebounds and separates from the test sample. The indentation amount H into the test sample S by the impact application member 10 as illustrated by FIG. 3 is also successively measured by the displacement meter 6. The impact force measured by the load meter 5 and the indentation amount H measured by the displacement meter 6 are input into the calculation unit 8. This indentation amount H differs depending on the physical properties of the rubber.

Figure 4:
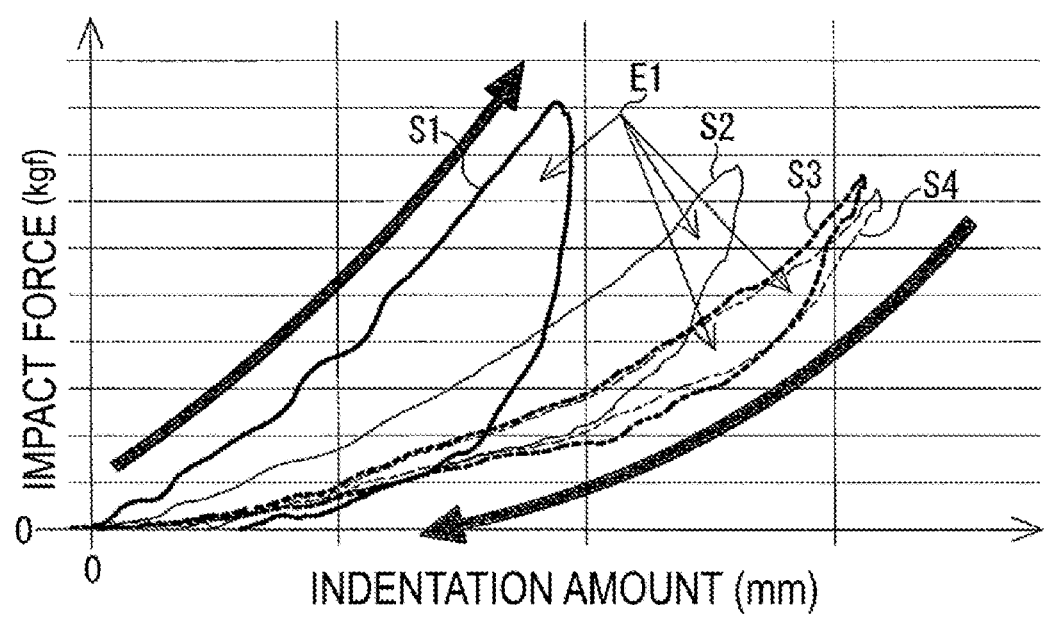
FIG. 4 is a graph illustrating the relationship between the impact force and indentation amount at room temperature.
Figure 5:
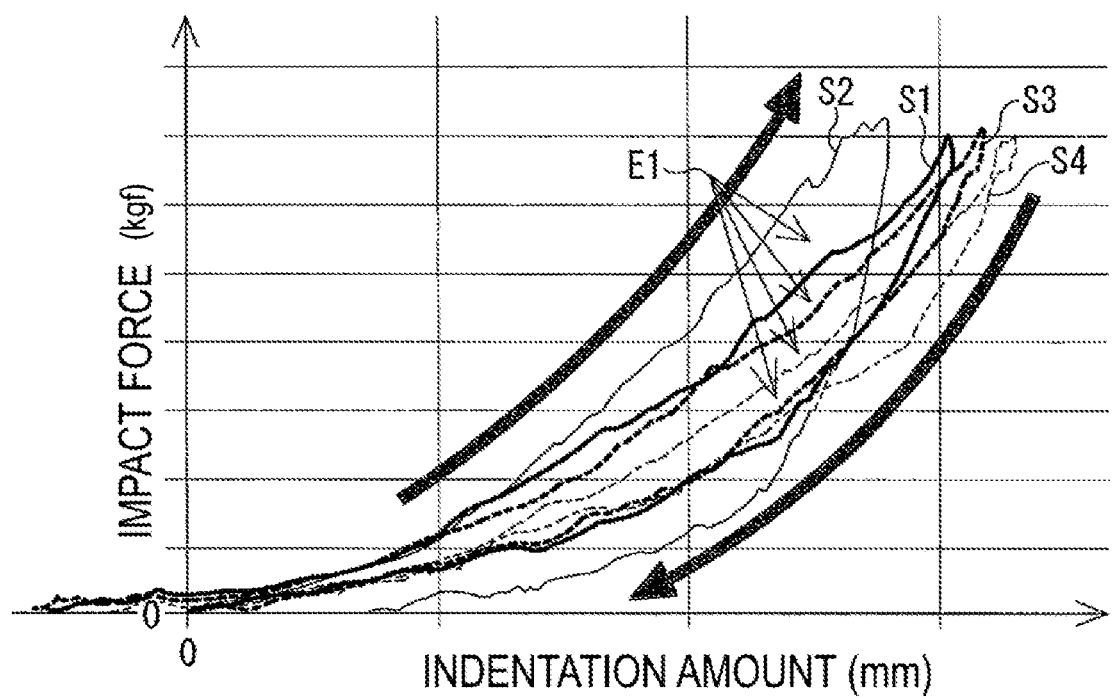
FIG. 5 is a graph illustrating the relationship between the impact force and indentation amount at 70° C.

As illustrated in FIGS. 4 and 5, the impact force and indentation amount H are measured by this impact test. FIG. 4 shows measurement data for a case in which four types of test samples S (S1 to S4) were tested at room temperature under the same test conditions (with the test sample S at a temperature of around 20° C.). FIG. 5 shows measurement data for a case in which only the temperature of the four types of test samples S (S1 to S4) was changed to 70° C. and the test was conducted.

The loss energy E1 absorbed by the test sample S when the impact application member 10 and the test sample S collide is calculated by the calculation unit 8 on the basis of the measurement data that was input. In FIGS. 4 and 5, the range of increase to the right of the data curves of each of the test samples S shows the relationship between the impact force and indentation amount H from when the impact application member 10 contacts the test sample S until the deepest indentation is reached. Therefore, the indentation energy Ea can be calculated by integrating the data curve in this range.

On the other hand, the range of decrease to the left of these data curves shows the relationship between the impact force and indentation amount H from when the impact application member 10 reaches the deepest indentation in the test sample S until the impact application member 10 rebounds and separates from the test sample S. Therefore, a repulsion energy Eb can be calculated by integrating the data curve in this range.

Accordingly, the loss energy E1 absorbed by the test sample S can be calculated by subtracting the repulsion energy Eb from the indentation energy Ea (E1=Ea−Eb). That is, in FIGS. 4 and 5, the surface area surrounded by the respective data curves S1, S2, S3, S4 becomes the loss energy E1 of the respective test samples S. This loss energy E1 (or the (loss energy E1)/(impact energy E)) differs depending on the rubber physical properties.

When the data of FIGS. 4 and 5 are compared, it is clear that the loss energy E1 is dependent on the temperature of the test sample S. Therefore, preferably, the impact test is carried out with the temperature of the test samples S being varied to a plurality of levels to thereby acquire each measurement data described above and understand the temperature dependency of the loss energy E1.

Figure 6:
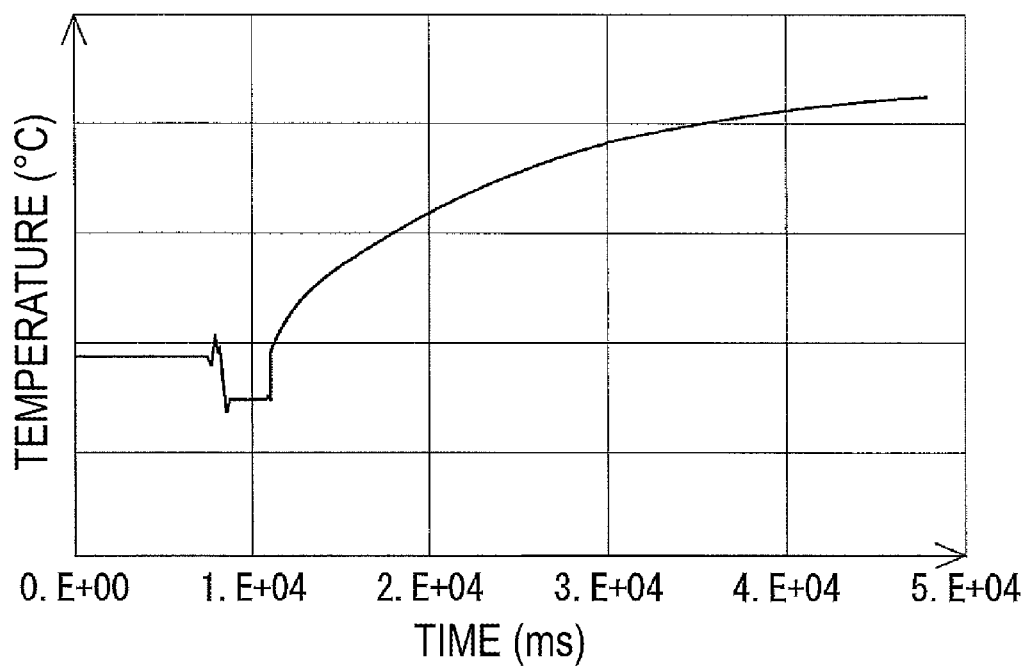
FIG. 6 is a graph illustrating the change over time of the surface temperature of a test sample.

With this impact test device 1, the surface temperature of the test sample S immediately after the impact application member 10 has rebounded can be successively measured by the temperature sensor 7. The surface temperature measured by the temperature sensor 7 is input into the calculation unit 8. As illustrated by FIG. 6, the surface temperature of the test sample at room temperature is measured, and the change in temperature over time can be understood.

The thermal energy E2 generated at the test sample S when the impact application member 10 and the test sample S collide is calculated by the calculation unit 8 on the basis of the measured surface temperature and indentation amount H. The thermal energy E2 can be calculated by $E2 = mc\Delta T$. Here, m is the mass of the test sample S for which the temperature has increased, c is the specific heat of the test sample S, and $\Delta T$ is the increase in temperature of the test sample S.

The increase in temperature $\Delta T$ (maximum increase in temperature $\Delta T$) of the test sample S due to collision with the impact application member 10 can be determined from the measurement data of FIG. 6. The specific heat c of the test sample S is determined in advance.

The mass m of the test sample S that has increased in temperature is calculated, for example, as follows. The indentation amount H by the impact application member 10 is measured by the displacement meter 6. Furthermore, the shape of the impact application member 10 is determined in advance, and therefore for example, a volume V calculated by multiplying the maximum cross-sectional area of the indented portion of the test sample S when indented at a maximum depth by the impact application member 10, by the maximum indentation amount H is used as the volume V of the test sample S that has increased in temperature. The specific gravity p of the test sample S is already determined in advance, and therefore the mass m of the test sample S that has increased in temperature can be calculated by multiplying the volume V by the specific gravity p. Furthermore, the thermal energy E2 can be calculated by multiplying the mass m, the specific heat c, and the increase in temperature $\Delta T$. This thermal energy E2 differs depending on the rubber physical properties.

After the impact test has been conducted and data of necessary items have been acquired, as illustrated in FIG. 1, a relative evaluation of the plurality of types of test samples S on which the impact test was conducted is performed with respect to each of the items for which data was acquired (loss energy E1, thermal energy E, and indentation amount H).

The specific relative evaluation method ranks the superiority of the plurality of test samples S with respect to the items for which data was acquired. Regarding the loss energy E1, for example, as the loss energy E1 becomes larger, the impact resistance is evaluated as becoming superior, and thus a superiority ranking of first place, second place, third place and fourth place is assigned in order from the largest loss energy E1. Regarding the thermal energy E2, for example, as the thermal energy E2 becomes larger, the impact resistance is evaluated as becoming superior, and thus a superiority ranking (first place to fourth place) is assigned in order from the largest thermal energy E2. Regarding the indentation amount H, for example, as the indentation amount H becomes smaller, the flaw depth becomes smaller, and therefore the impact resistance is evaluated as becoming superior. Therefore, a superiority ranking (first place to fourth place) is assigned in order from the smallest indentation amount H.

Next, as illustrated in FIG. 1, a comprehensive evaluation of each test sample is conducted. In this comprehensive evaluation, a specific test sample S is selected from the plurality of types of test samples S1 to S4 based on the ranking assigned as described above. In a case where data was acquired for only one item, the test sample S with the highest superiority ranking (first place) with respect to that item is identified, and this sample S is selected.

In a case where data was acquired for a plurality of items, the priority order between each preset item is set in advance. For example, a ranking is set in the order of the loss energy E1, the indentation amount H, and the thermal energy E2 for the item with the highest priority order. Furthermore, a specific optimal test sample S (rubber) is selected from the plurality of types of test samples S1 to S4 on the basis of the ranking of the superiority of the plurality of types of test samples S with respect to each item and a priority order between respective preset items.

More specifically, in a case where a certain test sample S1 has the highest superiority with respect to all of the items, the test sample S1 thereof is selected. However, there are also cases in which a certain test sample S2 has the highest superiority with respect to the loss energy E1 item, but other test samples S1 and S3 have the highest superiority with respect to the indentation amount H item and the thermal energy E2 item. In such a case, emphasis is placed on the ranking of the test samples S with respect to the item with the highest priority order (loss energy E1), and therefore the test sample S2 is selected.

In this manner, with the present technology, data is acquired for at least one of three above-described items closely related to the durability (impact resistance) of rubber including the loss energy E1, the thermal energy E2 and the indentation amount H, and the data thereof is used. Therefore, by selecting the optimal rubber on the basis of the ranking of superiority of the plurality of types of test samples S with respect to these items, an appropriate rubber (upper cover rubber) that conforms to the actual use of the target object (conveyor belt) can be selected.

According to the present technology, an appropriate upper cover rubber can be selected in accordance with the life span of the conveyor belt. In addition, an upper cover rubber which can suppress flaw depth to within a tolerance range can also be selected. When a selection is made using the data of the above-described three items, an appropriate rubber (upper cover rubber) that conforms to the actual use with good precision can be easily selected.

Next, another embodiment of the rubber selection method of present technology is described.

With the above-described embodiment, an impact test is performed using a plurality of test samples S when selecting an appropriate rubber. However, with the present embodiment, when an appropriate rubber is to be selected, an impact test is not implemented, and data that has been accumulated through impact tests that have already been conducted is used.

Therefore, with the present embodiment, at least one of the three items of data described with the previous embodiment including the loss energy E1, the thermal energy E2 and the indentation amount H is acquired, and the correlation between the item(s) for which data was acquired and the viscoelastic characteristics of each test sample S is understood in advance. As the viscoelastic characteristic, the coefficient of loss (tan δ), the storage elastic modulus (E'), the loss elastic modulus (E"), and the like can be used.

The ranking order of the superiority of the plurality of types of test samples S with respect to the items for which data was acquired is understood in advance. More specifically, regarding the loss energy E1, for example, as the loss energy E1 becomes larger, the impact resistance is evaluated as becoming superior, and thus the test samples S are ranked in order of superiority with the largest loss energy E1 being the most superior. Regarding the thermal energy E2, for example, as the thermal energy E2 becomes larger, the impact resistance is evaluated as becoming superior, and thus the test samples S are ranked in order of superiority with the largest thermal energy E2 being the most superior. Regarding the indentation amount H, for example, as the indentation amount H becomes smaller, the flaw depth becomes smaller, and therefore the impact resistance is evaluated as becoming superior.

In this manner, a database which indicates the correlation with the viscoelastic characteristic of each test sample S is prepared, and is stored in a computer or other such calculation device. Furthermore, the ranking order of the superiority of the plurality of types of test samples S with respect to each item is associated with this database. In addition, the data of each item is temperature dependent, and therefore a database is preferably prepared for each prescribed temperature.

Figure 7:
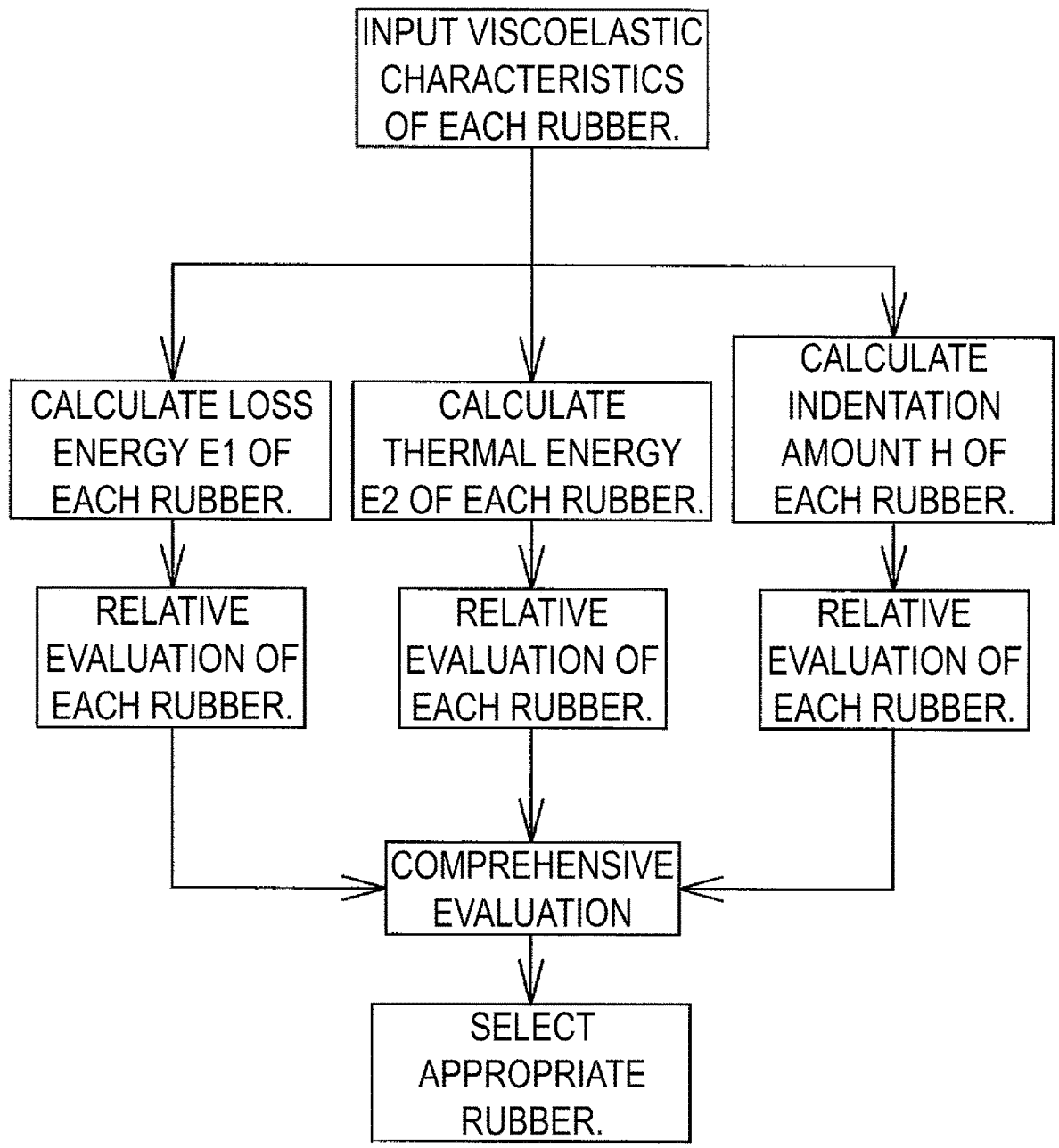
FIG. 7 is an explanatory diagram (flowchart) illustrating the flow when selecting an appropriate rubber according to another embodiment of the present technology.

Next, as illustrated in FIG. 7, when an appropriate rubber is to be selected for the upper cover rubber, the viscoelastic characteristics of the plurality of types of rubber candidates are input into the calculation device. A specific rubber is selected by the calculation device from amongst the plurality of types of rubber candidates on the basis of the viscoelastic characteristics that were input, and the above-described correlation and ranking order.

More specifically, the data for each item is calculated with respect to each rubber using the correlation understood in advance between the viscoelastic characteristics and each item (loss energy E1, thermal energy E2, and indentation amount H), and the values of the viscoelastic characteristics that were input. Through this, the loss energy E1, thermal energy E2 and the extent of the indentation amount H of each rubber are determined.

Next, the superiority of each rubber is relatively evaluated based on the ranking order understood in advance for each item. Through this, the order of superiority with each item is determined.

Next, the individually evaluated rubbers are comprehensively evaluated. The priority order between each item is set in advance. For example, a ranking is set in the order of the loss energy E1, the indentation amount H, and the thermal energy E2 for the item with the highest priority order.

In the comprehensive evaluation, in a case where a certain rubber has the highest superiority with respect to all of the items, the rubber thereof is selected. However, there are also cases in which a certain rubber has the highest superiority with respect to the loss energy E1 item, but another rubber also has the highest superiority with respect to the indentation amount H item and the thermal energy E2 item. In such a case, emphasis is placed on the ranking of the rubbers with respect to the item with the highest priority order (loss energy E1), and therefore the rubber with the highest superiority with respect to the loss energy E1 is selected.

In each of the embodiments described above, cases in which the target object is a conveyor belt, and the rubber to be selected is used as the upper cover rubber were described as examples, but the present technology is not limited thereto. Other examples of the rubber selected using the present technology include a lower cover rubber for a conveyor belt, tread rubber for a tire, etc.

The invention claimed is:

1. A rubber selection method for selecting a rubber for use in a target object to be used while being collided against by a colliding object, wherein
an impact test in which an impact application member is made to free fall onto a test sample of a plurality of types of rubbers having different physical properties is performed under prescribed test conditions;
data for at least one of three items including a loss energy that is absorbed by the test sample when the impact application member collides with the test sample, a thermal energy that is generated at the test sample, and an indentation amount into the test sample by the impact application member is acquired; and
a specific test sample is selected from the plurality of types of test samples on a basis of a ranking of superiority of the plurality of test samples with respect to the item(s) for which data was acquired.

2. The rubber selection method according to claim 1, wherein data of the three items is acquired, and an optimal test sample is selected from the plurality of types of test samples on the basis of the ranking of the superiority of the plurality of types of test samples with respect to each item and a priority order between respective preset items.

3. The rubber selection method according to claim 1, wherein the physical properties include at least a viscoelastic characteristic.

4. A rubber selection method for selecting a rubber for use in a target object to be used while being collided against by a colliding object; wherein
an impact test in which an impact application member is made to free fall onto a test sample of a plurality of types of rubbers having different physical properties is performed under prescribed test conditions;
data for at least one of three items including a loss energy that is absorbed by the test sample when the impact application member collides with the test sample, a thermal energy that is generated at the test sample, and an indentation amount into the test sample by the impact application member is acquired;
a correlation between the item(s) for which data was acquired and a viscoelastic characteristic of each test sample, and a ranking order of the superiority of the plurality of types of test samples with respect to the item(s) for which data was acquired are understood in advance; and
when a rubber is to be selected, a specific rubber is selected from the plurality of types of candidate rubbers on a basis of the viscoelastic characteristics of the plurality of types of candidate rubbers, and the correlation and ranking order that are understood in advance.

5. The rubber selection method according to claim 1, wherein the target object is a conveyor belt.

6. The rubber selection method according to claim 2, wherein the physical properties include at least a viscoelastic characteristic.

7. The rubber selection method according to claim 6, wherein the target object is a conveyor belt.

8. The rubber selection method according to claim 4, wherein the target object is a conveyor belt.

* * * * *